(12) United States Patent
Greenstein

(10) Patent No.: US 8,507,251 B2
(45) Date of Patent: Aug. 13, 2013

(54) **MEDIUM AND METHOD FOR CULTURING *MYCOBACTERIUM AVIUM* SUBSPECIES *PARATUBERCULOSIS***

(76) Inventor: Robert J. Greenstein, Tenafly, NJ (US)

( * ) Notice: Subject to any disclaimer, the term of this patent is extended or adjusted under 35 U.S.C. 154(b) by 263 days.

(21) Appl. No.: 12/892,039

(22) Filed: Sep. 28, 2010

(65) Prior Publication Data

US 2011/0076746 A1    Mar. 31, 2011

Related U.S. Application Data

(60) Provisional application No. 61/246,227, filed on Sep. 28, 2009.

(51) Int. Cl.
*C12N 1/12*    (2006.01)
(52) U.S. Cl.
USPC ...................................... 435/253.1
(58) Field of Classification Search
None
See application file for complete search history.

(56) References Cited

U.S. PATENT DOCUMENTS 4,735,899 A * 4/1988 Stuart et al. ..................... 435/29

OTHER PUBLICATIONS

Merkal et al. "Comparison of *Mycobacterium paratuberculosis* and Other Mycobacteria, Using Standard Cytochemical Tests" American Journal of Veterinary Research Mar. 1966; 27 ( 117) : 519-21.*
Cosnes et al. "Effects of Current and Former Cigarette Smoking on the Clinical Course of Crohn's Disease" Alimentary Pharmacology & Therapeutics 1999 vol. 13: 1403-1411.
Kane et al. "Tobacco Use is Associated with Accelerated Clinical Recurrence of Crohn's Disease After Surgically Induce Remission" Journal of Clinical Gastroenterology 2005 vol. 39(1): 32-35.
Lewis et al. "Estimating Risks of Common Complex Diseases Across Genetic and Environmental Factors: the Example of Crohn Disease" Journal of Medical Genetics 2007 vol. 44: 689-694.
Naser et al. "Effect of Nicotine on Inflammatory Bowel Disease" American Journal of Gastroenterolgy 2001 vol. 96(12): 3455-3457.
Regueiro et al. "Cigarette Smoking and Age at Diagnosis of Inflammatory Bowel Disease" Inflammatory Bowel Diseases 2005 vol. 11(1): 42-47.

* cited by examiner

*Primary Examiner* — Jon P Weber
*Assistant Examiner* — Thane Underdahl
(74) *Attorney, Agent, or Firm* — Licata & Tyrrell, P.C.

(57) ABSTRACT

The present invention provides a growth medium and kit containing a nicotine analog and use of the same in a method for enhancing the growth of *Mycobacterium avium* subspecies *paratuberculosis* (MAP).

10 Claims, 2 Drawing Sheets

MEDIUM AND METHOD FOR CULTURING *MYCOBACTERIUM AVIUM* SUBSPECIES *PARATUBERCULOSIS*

This application claims the benefit of priority from U.S. Provisional Ser. No. 61/246,227 filed Sep. 28, 2009, which is incorporated herein in its entirety.

BACKGROUND OF THE INVENTION

The use of tobacco products has empirically observed, disparate effects in inflammatory bowel disease (IBD) (Birrenbach & Bocker (2004) *Inflamm. Bowel Dis.* 10:848-859; Karban & Eliakim (2007) *World J. Gastroenterol.* 13:2150-2152; Regueiro, et al. (2005) *Inflamm. Bowel Dis.* 11:42-47). Crohn's disease (CD) (Dalziel (1913) *Br. Med. J.* ii:1068-1070; Crohn, et al. (1932) *J. Amer. Med. Assoc.* 99:1323-1328) is exacerbated by the use of tobacco products (Regueiro, et al. (2005) supra; Cosnes, et al. (1999) *Aliment Pharmacol. Ther.* 13:1403-1411; Lewis, et al. (2007) *J. Med. Genet.* 44:689-694). In contrast, the clinical course of ulcerative colitis (UC) is ameliorated by use of tobacco (Regueiro, et al. (2005) supra; Aldhous, et al. (2007) *Am. J. Gastroenterol.* 102:589-597; Beaugerie, et al. (2001) *Am. J. Gastroenterol.* 96:2113-2116), or nicotine (Pullan, et al. (1994) *N. Engl. J. Med.* 330:811-815; McGrath, et al. (2004) *Cochrane Database Syst. Rev.*:CD004722) one of tobacco's 4000 constituent molecules (Dube & Green (1982) 36$^{th}$ Tobacco Chemists Research Conference. Symposium on the Formation, Analysis and Composition of Tobacco Smoke, Raleigh N.C. pp. 42-102; Jenkins, et al. (2000) The Chemistry of Environmental Tobacco:Composition and Measurement; Eisenberg (ed.) Boca Raton Fla.:CRC Press). The mechanism(s) involved although intensively investigated (Aldhous, et al. (2009) *PLoS ONE* 4:e6285; Nielsen, et al. (2009) *PLoS ONE* 4:e6210) is not understood (Karban & Eliakim (2007) supra), but is assumed to be due to the most bioactive component of tobacco; nicotine (Karban & Eliakim (2007) supra; Aldhous, et al. (2009) supra). It is of note that in a prior study, involving a solitary MAP strain, pure nicotine inhibited MAP growth in culture (Naser, et al. (2001) *Am. J. Gastroenterol.* 96:3455-3457).

The etiology of CD and UC is (are) not known. *Mycobacterium avium* subspecies *paratuberculosis* (MAP), causes a chronic wasting diarrheal disease in cattle called Johne's disease (Johne & Frothingham (1895) *Dtsch. Zeitschr. Tiermed., Vergl. Pathol.* 21:438-454), that is evocative of CD. Humans are continually exposed to viable MAP (Mishina, et al. (1996) *Proc. Natl. Acad. Sci. USA* 93:9816-9820; Ellingson, et al. (2005) *J. Food Prot.* 68:966-972; Grant, et al. (2002) *Appl. Environ. Microbiol.* 68:602-607; Ayele, et al. (2005) *Appl. Environ. Microbiol.* 71:1210-1214). There is increasing concern that MAP may be zoonotic (Greenstein & Collins (2004) *Lancet* 364:396-397; Greenstein (2003) *Lancet Infect. Dis.* 3:507-514; Greenstein, et al. (2009) In: Fratamico et al. (eds.) Sequelae and Long-Term Consequences of Infectious Diseases. One ed. Washington, ASM Press. American Society for Microbiology pp. 135-168). In contrast to leprosy, where *M. leprae* has never been grown in vitro (Stewart-Tull (1982) In: Ratledge & Stanford (eds.) The Biology of the *Mycobacteria*, Volume 1: Physiology, Identification, and Classification. One ed. New York, Academic Press. pp. 273-307), MAP has been cultured from humans with CD (Chiodini, et al. (1986) *J. Clin. Microbiol.* 24:357-363; Chiodini, et al. (1984) *J. Clin. Microbiol.* 20:966-971; Naser, et al. (2004) *Lancet* 364:1039-1044; Naser, et al. (2000) *Am. J. Gastroenterol.* 95:1094-1095; Bull, et al. (2003) *J. Clin. Microbiol.* 41:2915-2923) as well as patients with UC (aser, et al. (2004) supra).

There is an emerging explanation as to why this probable MAP zoonosis has not been appreciated. It is that multiple agents used in the treatment of IBD are in fact anti-MAP antibiotics. They are conventionally called "anti-inflammatories" (Greenstein, et al. (2007) *PLoS ONE* 2:e516) and "immuno modulators" (Shin & Collins (2008) *Antimicrob. Agents Chemother.* 52:418-426; Greenstein, et al. (2009) *Int. J. Infect. Dis.* 13:e254-263; Greenstein, et al. (2007) *PLoS ONE* 2:e161; Greenstein, et al. (2008) *PLoS ONE* 3:e249). Analogous to the multiple clinical manifestations of leprosy (Greenstein, et al. (2009) supra; Ridley & Jopling (1962) *Lepr. Rev.* 33:119-128; Ridley & Jopling (1966) *Int. J. Lepr. Other Mycobact. Dis.* 34:255-273), it has been suggested that all of IBD may be caused MAP (Mishina, et al. (1996) supra; Greenstein, et al. (2009) supra; Naser, et al. (2004) supra).

In many cases, the detection of MAP in living tissue, food, and water requires first culturing the bacterium. Even though MAP is hardy, it is slow growing and fastidious, which means it is difficult to culture. To facilitate detection of MAP, improved culturing methods are needed. The present invention addresses this need in the art by providing a culture medium which enhances the growth of MAP thereby facilitating its detection in food, water, and other biological samples.

SUMMARY OF THE INVENTION

The present invention features a method for enhancing the growth of MAP by culturing MAP in the presence of a nicotine analog. In some embodiments, the nicotine analog has the structure wherein $R_1$ is $NH_2$ or O and $R_2$ is absent, or a ribose or nucleotide group. In particular embodiments, the nicotine analog is nicotinic acid, nicotinamide, α-NAD, or β-NAD. In yet other embodiments, the MAP is from a biological sample.

The present invention also features a growth medium and kit containing at least one nicotine analog for use in enhancing the growth of MAP.

BRIEF DESCRIPTION OF THE DRAWINGS

FIG. 1 depicts the cumulative Growth Index (cGI) of MAP strain Dominic in the presence of nicotine, nicotinic acid, α-nicotinamide adenine dinucleotide (NAD), β-NAD, and isoniazid, expressed as.

DETAILED DESCRIPTION OF THE INVENTION

Figure 1:
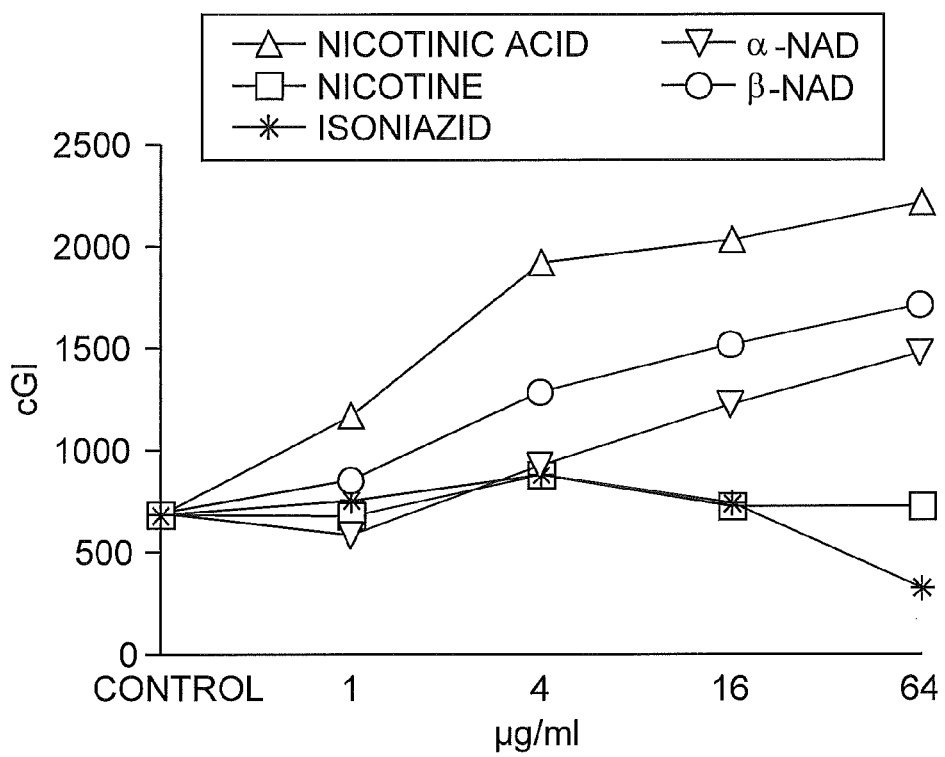
Figure 2:
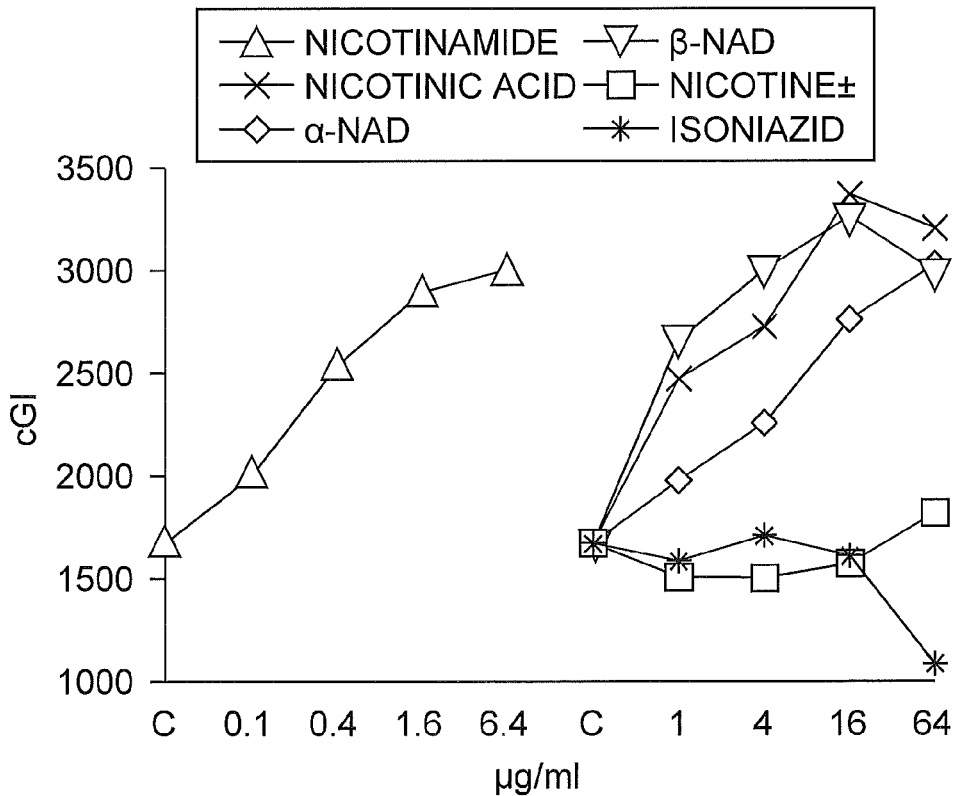
FIG. 2 depicts the depicts the cumulative Growth Index (cGI) of MAP strain UCF-4 in the presence of nicotine, nicotinic acid, nicotinamide, α-NAD, β-NAD, and isoniazid as compared to control (C).
Figure 3:
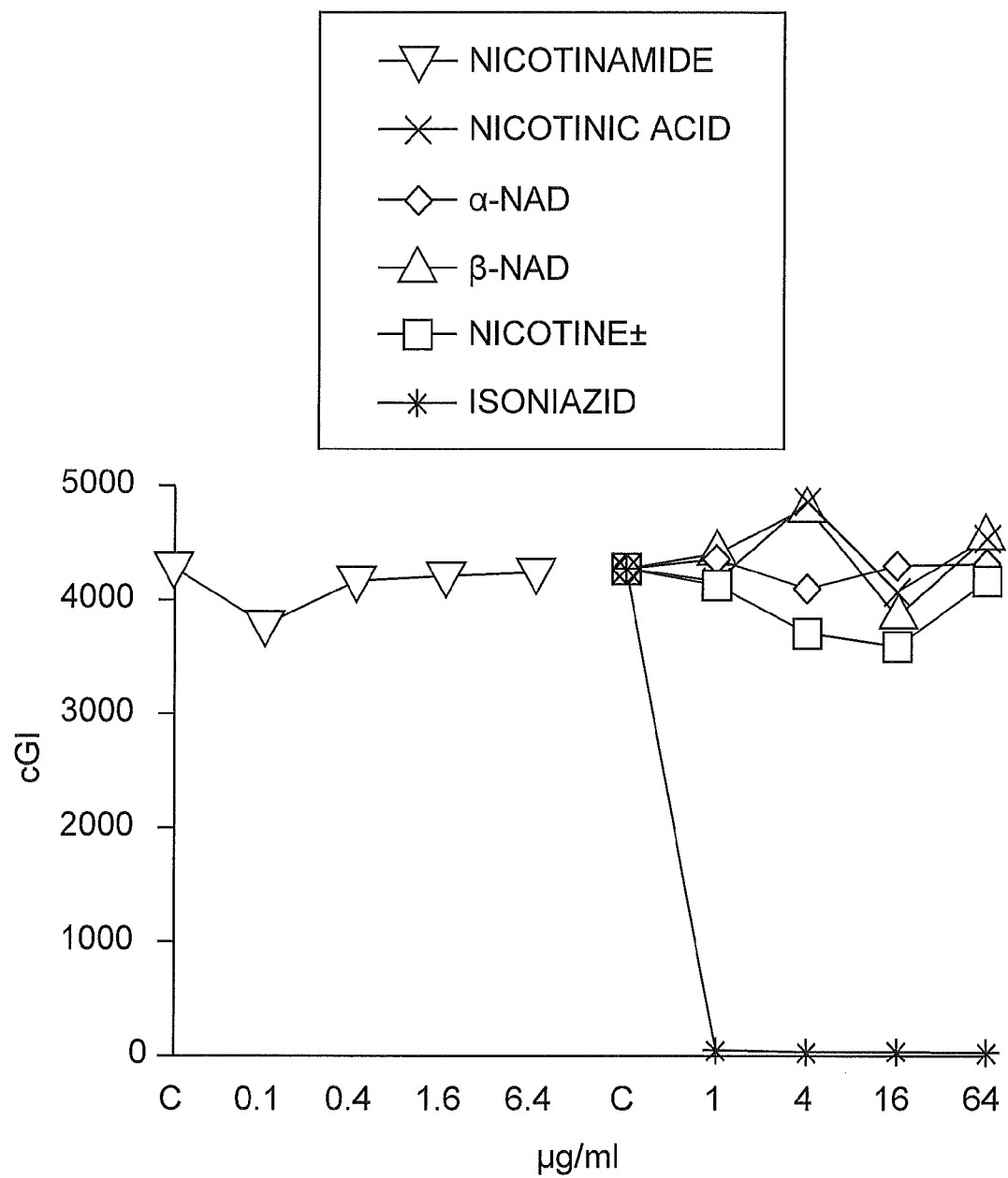
FIG. 3 shows the cumulative Growth Index (cGI) growth of *M. tuberculosis* in the presence of nicotine, nicotinic acid, nicotinamide, α-NAD, β-NAD, and isoniazid as compared to control (C).

Tobacco use has been shown to exacerbate Crohn's disease and its cessation results in clinical improvement (Kane, et al. (2005) *J. Clin. Gastroenterol.* 39(1):32-5). Therefore, it was determined whether nicotine, or its structural analogs could modify MAP growth kinetics in vitro. In this analysis, MAP was grown in the presence of varying concentrations of nicotine, isoniazid, nicotinic acid, nicotinamide, α-NAD, and β-NAD. The results of this analysis indicated that while nicotine had no effect on the growth kinetics at the concentrations tested, nicotine structural analogs, nicotinic acid, nicotinamide, α-NAD, and β-NAD, profoundly effected the growth kinetics of multiple strains of MAP including Dominic (FIG. 1) and UCF-4 (FIG. 2). In contrast, nicotine and its structural analogs provided no enhancement in the growth of *M. tuberculosis* complex (FIG. 3). In light of these results, nicotine analogs find use in the selective enhancement of MAP growth in vitro.

Thus, the present invention embraces a MAP culture medium, kit and method for enhancing the growth of MAP. According to the method of the invention, MAP is cultured in the presence of a nicotine analog so that growth of MAP is enhanced. For the purposes of the present invention, culturing of MAP refers to the growth of MAP bacterium in vitro in a solid, semi-solid or liquid medium. While exemplary media are provided herein, it is contemplated that any medium known in the art to support the growth of MAP can be supplemented with one or more nicotine analogs according to the present invention.

Culturing of MAP can be for various purposes including, but not limited to, the identification of anti-MAP agents, the detection of MAP in biological samples, the diagnosis of a MAP infection, as well as in research of morphological, physiological and molecular biological aspects of MAP. As such, MAP can be obtained from a variety of sources, including biological samples such as food, water, blood, a stool sample, cerebrospinal fluid or alternatively a biopsy sample, e.g., lesioned central nervous tissue or a biopsy obtained in endoscopy or a surgically ressected specimen. In vitro culturing of MAP bacterium generally involves placing the sample on an appropriate growth medium under conditions suitable for growth of MAP. By way of illustration, MAP can be obtained by harvesting a tissue sample from a subject suspected of having a MAP infection (e.g., a subject suspected of having Crohn's disease, inflammatory bowel disease, Multiple Sclerosis or Alzheimer's Disease), washing the tissue sample with phosphate-buffered saline (e.g., 0.067 M, pH 6.8) and resuspending the sample in albumin. The sample is then inoculated into MGIT media (Becton Dickinson, Palo Alto, Calif.) supplemented with a nicotine analog, and the medium is incubated at 37° C. until MAP growth is detected.

The instant method is said to enhance MAP growth in that supplementation of a growth medium with a nicotine analog provides at least a 20%, 30%, 40%, 50%, 60%, 70%, or 80% increase in growth as compared to a control, e.g., MAP not growth in the presence of a nicotine analog. As described herein, growth enhancement can be determined and expressed as cumulative Growth Index.

As used in the context of the present invention, a "nicotine analog" is intended to mean a compound having the structure of Formula I.

wherein $R_1$ is $NH_2$ or O; and $R_2$ is absent, or a ribose group or nucleotide group. Nucleotide groups encompassed within the scope of the invention include, but are not limited to, adenine dinucleotide or mononucleotide groups.

Exemplary nicotine analogs embraced by the invention include:

Nicotinic Acid    Nicotinamide

β-NAD

α-NAD

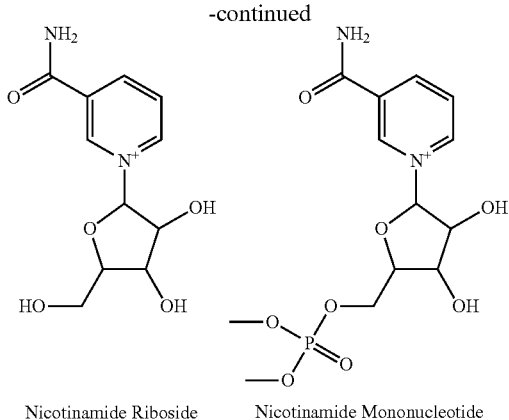

-continued

Nicotinamide Riboside

Nicotinamide Mononucleotide

Nicotine analogs can be used at any appropriate amount, which may be dependent upon the analog selected. Particularly desirable amounts of nicotine analogs used in the culture of MAP are in the range of 50 ng/mL to 100 μg/mL. The selection of an appropriate amount can be based upon the data presented herein or by additional dose-response analyses.

As indicated, once MAP has been cultured under the conditions described herein, it can be used for various purposes including research, diagnosis and the identification of anti-MAP agents for use in the prevention and/or treatment of a MAP infection. In this respect, the instant invention further include a determination of antibiotic susceptibility to effectively select a treatment regime for a subject from which a sample originated. To determine antibiotic susceptibility, the in vitro cultured MAP is contacted with a plurality of antibiotics (e.g., 2, 3, 4, 5, 10, or more). Antibiotic susceptibility testing can be carried out using, e.g., the MIGT or BACTEC systems (both Becton-Dickerson), or ESP II (Trek Diagnostic Systems, Cleveland, Ohio). While the BACTEC system is not highly automated and uses a radionucleotide ($^{14}C$), this system is sensitive as it uses a medium that is not very rich and therefore the antibiotics are not idiosyncratically absorbed onto the proteins in the medium.

Having demonstrated that nicotine analogs enhance the growth of MAP, another feature of the present invention is a growth medium for enhancing the growth of MAP. The medium of the present invention includes a base growth medium in admixture with one or more nicotine analogs described herein. For the purposes of the present invention, a base growth medium can be any medium known in the art to support the growth of MAP. Base growth media suitable for use in accordance with the invention include, but are not limited to, BACTEC 460TB or *Mycobacteria* Growth Indicator Tube (MIGT) media (Becton, Dickinson and Company, Cockeysville, Md.) as well as Middlebrook 7H9 broth enriched with oleic acid albumin dextrose complex, 0.4% casamino acids containing vitamins, 40 μg/ml tryptophan, 0.5 μg/ml, mycobactin J, and 0.05% TWEEN 80. See, e.g., Harrisa, et al. (2006) *FEMS Microbiol. Lett.* 175:21-26.

For use in the enhancement of MAP growth, particular embodiments feature the growth medium of the invention in the form of a kit. A kit according to the invention generally includes a base growth medium and one or more nicotine analogs described herein. The base growth medium and one or more nicotine analogs can be provided in separate containers or in a single container. The kit can further include other vitamins, proteins, minerals, sugars, or additives that support the growth of MAP. In addition, the kit can include instructions for mixing, sterilizing, and/or using the components of the kit. The kit can further include reagents, e.g., antibodies or primers, for detecting the presence of MAP.

The invention is described in greater detail by the following non-limiting examples.

EXAMPLE 1

Materials and Methods

In this study eight strains of mycobacteria were used, four of which were MAP. Two MAP strains had been isolated from humans with Crohn's disease. Dominic (ATCC 43545; Chiodini, et al. (1986) supra) and UCF 4 (Naser, et al. (2004) supra). The other two MAP strains were from ruminants with Johne's disease ATCC 19698 (ATCC Rockville, Md.) and 303. The *M. avium* subspecies *avium* strains (hereinafter called *M. avium*) were ATCC 25291 (veterinary source) and *M. avium* 101 (Bertram, et al. (1986) *J. Infect. Dis.* 154:194-195). To study the *M. tuberculosis* complex, two BioSafety level 2 strains, Bacillus Callmette Guerin (BCG) *M. bovis* Karlson & Lessel (ATCC 19015) and an avirulent *M. tb* strain; ATCC 25177 were used.

Because it renders clinically resistant strains of MAP inappropriately susceptible to antimicrobials in cell culture (Damato & Collins (1990) *Vet. Microbiol.* 22:31-42), or interferes with growth and susceptibility (Greenstein, et al. (2009) supra), the detergent TWEEN 80 (recommended to prevent mycobacterial clumping) was not used in cultures herein.

Cultures were processed according to conventional methods (Greenstein, et al. (2007) supra; Greenstein, et al. (2009) supra; Greenstein, et al. (2007) supra; Greenstein, et al. (2008) supra; Rastogi, et al. (1992) *Antimicrob. Agents Chemother.* 36:2843-2846; Greenstein, et al. (2009) *Gut Pathogens* 1:4). In brief, the radiometric $^{14}CO_2$ BACTEC® 460 system (Becton-Dickinson, Franklin Lakes, N.J.) was used. Each vial had the identical concentration of all constituents, except for the amount of test agent. Vials were assayed on a daily basis, quantifying the amount of $^{14}C$ released as $^{14}CO_2$, by the integral detector in the BACTEC 460. The data were obtained as a manufacturer determined, arbitrary Growth Units (GU) of 0-999.

In this study, agents were dissolved in either Middlebrook 7H9 broth (DIFCO®,: Sparks, Md.) or 18 MΩ distilled water. Chemicals were dissolved, aliquoted, stored at −80° C., thawed, used once and discarded. Each experiment was performed with agents that had been dissolved in only water (all nicotine related molecules) or 7H9 broth (salicylic acid & PAS.)

As experimental controls, two well-established antibiotics were used to inhibit mycobacterial growth. Isoniazid (INH; Iso Nicotino Hydrazide), used to treat *tuberculosis* (Noufflard & Deslandes (1952) *Ann. Inst. Pasteur.* (Paris) 83:769-773) and leprosy (Lowe (1952) *Lancet* 2:1012-1013) and para-amino salicylic acid (PAS) used to treat tuberculosis Lehmann (1946) *Lancet* 1:15-16). In 1940 Bernheim first reported the enhancement of growth of mycobacteria by salicylate (Bernheim (1940) Science 92:204). Accordingly, the experimental control for enhancement of growth was salicylic acid. Racemic (±) nicotine and it two enantiomers (+) and (−), were also analyzed, as were nicotinic acid, nicotinamide (Vitamin B3, an amide of nicotinic acid), and α- and β-nicotinamide adenine dinucleotide (α- and β-NAD.) (All Sigma, St Louis. MO). Agents were studied at concentrations ranging from 0.1 to 64 μg/ml.

For clarity and ease of understanding, data are presented in two ways; as the cumulative Growth Index (cGI) for an individual mycobacterium from a single experiment (see Figures)

and, alternatively, for a single chemical the same data from all experiments were recalculated and presented as the "percent change from control cGI" (see Tables). An increase was presented as "%+ΔcGI" and a decrease as "%−ΔcGI". See, Greenstein, et al. (2007) supra for calculation.

EXAMPLE 2

Use of Nicotine Analogs to Enhance Growth of MAP

The initial experimental control was salicylic acid, which showed a dose-dependant enhancement of growth for *M. avium* ATCC 25291 (104%+ΔcGI at 64 μg/ml) and *M. bovis* (BCG) (95%+ΔcGI at 64 μg/ml). In contrast, only one of four MAP strains showed dose-dependant enhancement; MAP: 303 (66%+ΔcGI at 64 μg/ml).

The inhibitory control was PAS (Lehmann (1946) supra), which exhibited bactericidal activity against *M. avium* and BCG (≧94%−ΔcGI at 4 (four) μg/ml). PAS exhibited dose-dependent inhibition on MAP 19698 and MAP 303 (80%−ΔcGI at 64 μg/ml).

The antibiotic inhibitory control for the structural analogs of nicotine was INH (Robitzek & Selikoff (1952) *Am. Rev. Tuberc.* 65:402-428). INH was bactericidal on *M. tb* (97%−ΔcGI at 1 (one) μg/ml) and had dose-dependent inhibition on BCG and *M. avium:* 101(≧97%−ΔcGI at 64 μg/ml) (Table 1) In contrast, at the doses tested, INH has no dose-dependent inhibition on any MAP strain, although inhibition occurred by 64 μg/ml against all four MAP strains (Table 1, FIGS. 1 and 2)

TABLE 1

| | MAP | | | | *M. avium* | | *M. tb* complex | |
|---|---|---|---|---|---|---|---|---|
| μg/ml | Dominic* | UCF-4 | 19698 | 303 | 25291 | 101 | BCG | Tb |
| 1 | 18%, 11% | −5% | −20% | −18% | 176% | −48% | −62% | −97% |
| 4 | 9%, 29% | 2% | −14% | −6% | 89% | −96% | −25% | −98% |
| 16 | −4%, 9% | −4% | −17% | −12% | 189% | −95% | −63% | −98% |
| 64 | −65%, −52% | −35% | −63% | −52% | −90% | −97% | −99% | −98% |

*Results from two experiments. Data are presented as percent increase (% ΔcGI) or decrease (% −ΔcGI) in cumulative Growth Index (cGI) from concomitant control. INH was dissolved in water.

Nicotine, whether racemic (±) or either of its enantiomers (+) or (−), had neither enhancement nor an inhibitory effect on any of the eight mycobacterial strains, when studied at 1-64 μg/ml (Table 2; FIGS. 1-3).

TABLE 2

| | MAP | | | | *M. avium* | | *M. tb* complex | |
|---|---|---|---|---|---|---|---|---|
| μg/ml | Dominic* | UCF-4 | 19698 | 303 | 25291 | 101 | BCG | Tb |
| 1 | −2%, 0% | −10% | −20% | 7% | 106% | 55% | −65% | 6% |
| 4 | 29%, 30% | −10% | −20% | 8% | 63% | 0% | −41% | −14% |
| 16 | 1%, 6% | −6% | −21% | −22% | 143% | 15% | −39% | −10% |
| 64 | −12%, 7% | 9% | −11% | 7% | 112% | 5% | −51% | 2% |

*Results from two experiments. Data are presented as percent increase (% ΔcGI) or decrease (% −ΔcGI) in cumulative Growth Index (cGI) from concomitant control. Nicotine was purchased in aqueous solution.

Nicotinic acid is a component of tobacco (Griffith, et al. (1960)*J. Biol. Chem.* 235:3536-3538; Weidel (1873) *Justus Liebig's Annalen der Chemie and Pharmacie* 165:328-349). Of the four non-MAP strains studied, nicotinic acid enhanced growth of *M. avium*, but not of the *M. tuberculosis* complex (Table 3, FIG. 3). Growth of MAP isolated from humans was enhanced by nicotinic acid (Dominic 225%+ΔcGI; UCF-4, 92%+ΔcGI, at 64 μg/ml; Table 3, FIGS. 1 and 2). MAP from bovine sources showed far less nicotinic acid induced enhancement than was observed with the human MAP isolates (Table 3).

TABLE 3

| | MAP | | | | *M. avium* | | *M. tb* complex | |
|---|---|---|---|---|---|---|---|---|
| μg/ml | Dominic* | UCF-4 | 19698 | 303 | 25291 | 101 | BCG | Tb |
| 1 | 46%, 71% | 48% | −17% | −4% | 98% | 41% | −45% | −1% |
| 4 | 133%, 181% | 63% | −4% | 2% | 170% | 47% | −61% | 29% |

TABLE 3-continued

| | MAP | | | | M. avium | | M. tb complex | |
|---|---|---|---|---|---|---|---|---|
| µg/ml | Dominic* | UCF-4 | 19698 | 303 | 25291 | 101 | BCG | Tb |
| 16 | 195%, 198% | 101% | 12% | −4% | 167% | 40% | −45% | 9% |
| 64 | 197%, 225% | 92% | 30% | 22% | 175% | 56% | −14% | 15% |

*Results from two experiments. Data are presented as percent increase (% ΔcGI) or decrease (% −ΔcGI) in cumulative Growth Index (cGI) from concomitant control. Nicotinic acid was dissolved in water.

Initially, nicotinamide was studied at the same concentration as the other agents. However, against Dominic, the effect was high (≧100%+ΔcGI for 1, 4, 16 and 64 µg/ml) and constant (Table 4, results from first experiment). Accordingly, 10-fold lower nicotinamide concentrations were used for the remaining experiments (Table 4, second Dominic experiment and remaining seven columns, FIGS. 2 and 3).

TABLE 4

| | MAP | | | | M. avium | | M. tb complex | |
|---|---|---|---|---|---|---|---|---|
| µg/ml | Dominic | UCF-4 | 19698 | 303 | 25291 | 101 | BCG | Tb |
| 0.1 | (1) 110%, 32% | 20% | −6% | −5% | 23% | 6% | −71% | −1% |
| 0.4 | (4) 115%, 98% | 52% | −2% | −28% | 105% | −21% | −19% | 11% |
| 1.6 | (16) 125%, 156% | 73% | −8% | 11% | 157% | 7% | −43% | 4% |
| 6.4 | (64) 106%, 156% | 79% | −7% | 3% | 144% | 58% | −42% | 10% |

Data are presented as percent increase (% ΔcGI) or decrease (%−ΔcGI) in cumulative Growth Index (cGI) from concomitant control. Nicotinamide was dissolved in water. Note that, uniquely for this study, the nicotinamide was studied at a 10-fold greater dilution than the other agents studied. The single exception is the index Dominic experiment (second data set), wherein the standard dilutions (shown in parentheses) were used.

For *M. avium* (25291 & 101), nicotinamide caused enhancement of growth (Table 4). In contrast, nicotinamide had no effect on the *M. tuberculosis* complex (BCG & *M. tb*) (Table 4, FIG. 3). Comparable to observations with nicotinic acid (Table 3), nicotinamide enhanced MAP isolated from humans, but had no effect on MAP isolated from ruminants (Table 4, FIG. 2).

Two molecules that contain nicotinamide as an integral component of their structure were also analyzed, α- and β-NAD. The human MAP isolates (Dominic & UCF-4), whose growth was enhanced by nicotinamide itself, were likewise enhanced by α-NAD (Dominic, 135%+ΔcGI; UCF-4, 81%+ΔcGI, at 64 µg/ml) and β-NAD (Dominic, 150%+ΔcGI; UCF-4, 79%+ΔcGI, at 64 µg/ml)(Tables 5 and 6, FIGS. 1 and 2). In contrast, α- and β-NAD had little or no effect on the other six strains studied, including the two MAP bovine isolates (Tables 5 and 6, FIG. 3).

TABLE 5

| | MAP | | | | M. avium | | M. tb complex | |
|---|---|---|---|---|---|---|---|---|
| µg/ml | Dominic* | UCF-4 | 19698 | 303 | 25291 | 101 | BCG | Tb |
| 1 | 25%, −16% | 18% | −16% | 8% | −2% | 39% | −51% | 2% |
| 4 | 79%, 35% | 35% | −6% | 9% | 160% | −15% | −60% | −6% |
| 16 | 104%, 78% | 65% | −17% | −8% | 131% | −21% | −50% | −1% |
| 64 | 135%, 115% | 81% | 13% | −18% | 147% | −14% | −48% | 0% |

*Results from two experiments. Data are presented as percent increase (% ΔcGI) or decrease (% −ΔcGI) in cumulative Growth Index (cGI) from concomitant control. α-NAD was dissolved in water.

TABLE 6

| | MAP | | | | M. avium | | M. tb complex | |
|---|---|---|---|---|---|---|---|---|
| µg/ml | Dominic* | UCF-4 | 19698 | 303 | 25291 | 101 | BCG | Tb |
| 1 | 13%, 24% | 59% | 5% | 18% | 123% | 18% | −72% | 20% |
| 4 | 60%, 87% | 79% | 23% | 34% | 66% | 24% | 1% | 21% |
| 16 | 130%, 122% | 95% | 6% | 18% | −37% | 27% | −47% | 9% |
| 64 | 114%, 150% | 79% | 8% | 1% | 42% | 22% | −59% | 14% |

*Results from two experiments. Data are presented as percent increase (% ΔcGI) or decrease (% −ΔcGI) in cumulative Growth Index (cGI) from concomitant control. β-NAD was dissolved in water.

In IBD, tobacco use results in paradoxical responses amongst patients who have CD or UC. These effects have no accepted mechanism of action. Because of different delivery methods and use patterns, the bioavailable dose of tobacco products that will occur in the human host will vary considerably (Pavia, et al. (2000) *J. Med. Microbiol.* 49:675-676). In this study, it was determined whether some of the ≧4000 molecules found in tobacco could perturb MAP growth, thereby providing a rational explanation for some tobacco related IBD effects.

Nicotine is the most commonly studied molecule associated with tobacco. Prior in vitro results are discordant. Enhanced growth of *M. tuberculosis, M. Kansasii, M. scrofulaceum, M. avium* and *M. intracellulare*, occurs at extremely high doses of nicotine (5 mg/ml) (Kotian, et al. (1984) *Ind. J. Tuberc.* 31:151-158). In contrast, inhibition of bacteria (including *M. phlei*) and fungal growth is observed at lower doses of nicotine (100-250 µg/ml) (Zelitch (1955) *J. Biol. Chem.* 216:553-575). Bactericidal inhibition of a single MAP strain was reported by 2 µg/ml nicotine (Naser, et al. (2001) supra), using the same BACTEC 460® system herein; however with supplementation of OADC (oleic acid, bovine serum albumin, dextrose and catalase). In this study, no effect on growth was observed for nicotine at 1-64 µg/ml on eight strains of three mycobacterial species.

Nicotinic acid is a naturally occurring constituent of tobacco (Griffith, et al. (1960) supra). The nicotinic acid dose-dependent enhancement observed herein occurred in all four MAP strains. However, the effect was most pronounced in the MAP strains isolated from humans. Additionally, nicotinic acid enhanced one *M. avium* strain, (25291). Nicotinamide is the amide of nicotinic acid. Both human MAP isolates were remarkably susceptible to nicotinamide growth enhancement. In contrast, neither of the bovine MAP isolates were enhanced at the dose of nicotinamide studied. Likewise, although *M. avium* growth was enhanced, nicotinamide had no effect on the representatives of the *M. tb.* complex. It was concluded that the enhanced response of mycobacteria to nicotinic acid and nicotinamide was both species-, as well as strain-, dependent.

Intact α-NAD enhanced MAP isolated from humans as well as *M. avium* 25291. β-NAD enhanced only the two human MAP isolates. Tobacco is particularly rich in the enzyme glycolic acid reductase (Zelitch (1955) supra). This enzyme reduces diphosphopyridine nucleotides to their constituent components (Zelitch (1953) *J. Biol. Chem.* 201:719-726; Zelitch & Ochoa (1953) *J. Biol. Chem.* 201:707-718). The glycolic acid reductase fraction of tobacco may, in vivo, cleave α- and (β-NAD to release nicotinamide. This could provide an additional, indirect, mechanism whereby tobacco products enhance the growth of MAP. Parenthetically, catalase markedly enhances the effect of glycolic acid reductase (Zelitch & Ochoa (1953) supra). This observation may, in part, account for the differences observed between the effect of nicotine in the present study and a prior study where catalase was added to the culture medium (Naser, et al. (2001) supra).

Overall, the analysis herein indicates that the use of tobacco, or its individual components, are compatible with either enhancement or inhibition of the growth of mycobacteria both in vitro and in vivo.

What is claimed is:

1. A method for enhancing the growth of *Mycobacterium avium* subspecies *paratuberculosis* (MAP) comprising culturing MAP in the presence of a nicotinic acid or derivatives thereof thereby enhancing the growth of MAP.

2. The method of claim 1, wherein the nicotinic acid or derivatives thereof has the structure wherein $R_1$ is $NH_2$ or OH and $R_2$ is absent, or a ribose or nucleotide group.

3. The method of claim 2, wherein the nicotinic acid or derivatives thereof is nicotinic acid, nicotinamide, α-nicotinamide adenine dinucleotide, or β-nicotinamide adenine dinucleotide.

4. The method of claim 1, wherein the MAP is from a biological sample.

5. A growth medium for enhancing the growth of *Mycobacterium avium* subspecies *paratuberculosis* (MAP) comprising a base growth medium to support the growth of MAP in admixture with at least one nicotinic acid or derivatives thereof.

6. The growth medium of claim 5, wherein the nicotinic acid or derivatives thereof has the structure wherein $R_1$ is $NH_2$ or OH and $R_2$ is absent, or a ribose or nucleotide group.

7. The growth medium of claim 6, wherein the nicotinic acid or derivatives thereof is nicotinic acid, nicotinamide, α-nicotinamide adenine dinucleotide, or β-nicotinamide adenine dinucleotide.

8. A kit comprising a base growth medium to support the growth of *Mycobacterium avium* subspecies *paratuberculosis* and at least one nicotinic acid or derivatives thereof.

9. The kit of claim 8, wherein the nicotinic acid or derivatives thereof has the structure wherein $R_1$ is $NH_2$ or OH and $R_2$ is absent, or a ribose or nucleotide group.

10. The kit of claim 9, wherein the nicotinic acid or derivatives thereof is nicotinic acid, nicotinamide, α-nicotinamide adenine dinucleotide, or β-nicotinamide adenine dinucleotide.

* * * * *